US012727869B2

(12) United States Patent
Jung et al.

(10) Patent No.: US 12,727,869 B2
(45) Date of Patent: Sep. 8, 2026

(54) RETRACTOR FOR SPINAL SURGERY

(71) Applicant: ENDOVISION CO., LTD., Daegu (KR)

(72) Inventors: Min Ho Jung, Daegu (KR); Sae Won Eum, Seoul (KR)

(73) Assignee: ENDOVISION CO., LTD., Daegu (KR)

( * ) Notice: Subject to any disclaimer, the term of this patent is extended or adjusted under 35 U.S.C. 154(b) by 1172 days.

(21) Appl. No.: 17/755,038

(22) PCT Filed: Jun. 25, 2020

(86) PCT No.: PCT/KR2020/008304
§ 371 (c)(1),
(2) Date: Aug. 17, 2022

(87) PCT Pub. No.: WO2021/080114
PCT Pub. Date: Apr. 29, 2021

(65) Prior Publication Data

US 2025/0345053 A1 Nov. 13, 2025

(30) Foreign Application Priority Data

Oct. 23, 2019 (KR) ........................ 10-2019-0132184

(51) Int. Cl.
*A61B 17/02* (2006.01)
*A61B 17/00* (2006.01)
*A61B 90/00* (2016.01)

(52) U.S. Cl.
CPC ...... *A61B 17/0218* (2013.01); *A61B 17/0206* (2013.01); *A61B 90/03* (2016.02);
(Continued)

(58) Field of Classification Search
CPC . A61B 17/0218; A61B 17/0206; A61B 90/03; A61B 2090/036; A61B 2017/00862; A61B 17/02
See application file for complete search history.

(56) References Cited

U.S. PATENT DOCUMENTS 5,030,224 A * 7/1991 Wright ................ A61B 17/083
600/209
6,702,739 B2 * 3/2004 Levisman ................ A61B 1/24
600/237
(Continued)

FOREIGN PATENT DOCUMENTS

KR 20-0241847 Y 10/2001
KR 10-2006-0107507 A 10/2006
KR 10-2013-0006588 A 1/2013

OTHER PUBLICATIONS

International Search Report for corresponding International application No. PCT/KR2020/008304; dated Apr. 1, 2021 (7 pages).

*Primary Examiner* — Eduardo C Robert
*Assistant Examiner* — Holly Joanna Lane
(74) *Attorney, Agent, or Firm* — Mendelsohn Dunleavy, P.C.

(57) ABSTRACT

The present invention relates to a retractor for spinal surgery, wherein the retractor is intended to secure and maintain a surgery hole during minimally invasive surgery (MIS) for spinal diseases. The retractor is characterized by comprising: a main body fastened to a surgery hole to maintain the surgery hole; an elastic means which provides the main body with a retraction force for maintaining the surgery hole; and a support member formed between the main body and the elastic means to transmit the retraction force to the main body. Accordingly, due to being provided with the elastic means that provides the main body with the retraction force for maintaining the surgery hole, the retractor does not need
(Continued)

to be controlled by medical personnel, is convenient to install in the surgery hole, has a simple structure, and hardly interferes with other medical devices, and thus is convenient to use.

10 Claims, 8 Drawing Sheets

(52) U.S. Cl.
CPC ............... *A61B 2017/00862* (2013.01); *A61B 2090/036* (2016.02)

(56) References Cited

U.S. PATENT DOCUMENTS

| | | | | |
|---|---|---|---|---|
| 6,964,675 | B2 * | 11/2005 | Zhu | A61B 17/10 606/108 |
| 8,211,012 | B2 | 7/2012 | Wing et al. | |
| 9,386,971 | B1 | 7/2016 | Casey et al. | |
| 10,299,670 | B1 * | 5/2019 | Sumaily | A61B 1/32 |
| 12,075,997 | B2 * | 9/2024 | Parker | A61B 17/02 |
| 2004/0024291 | A1 * | 2/2004 | Zinkel | A61B 17/0206 600/218 |
| 2006/0063978 | A1 * | 3/2006 | Ritland | A61B 17/02 600/213 |
| 2012/0220833 | A1 * | 8/2012 | Ehrenreich | A61B 17/0206 600/219 |
| 2020/0077997 | A1 * | 3/2020 | McCormick | A61B 17/0206 |

* cited by examiner 100
111
112
113
20
200
A 100
111
112
20
200
300
A 100
111
112
113
200
300
A

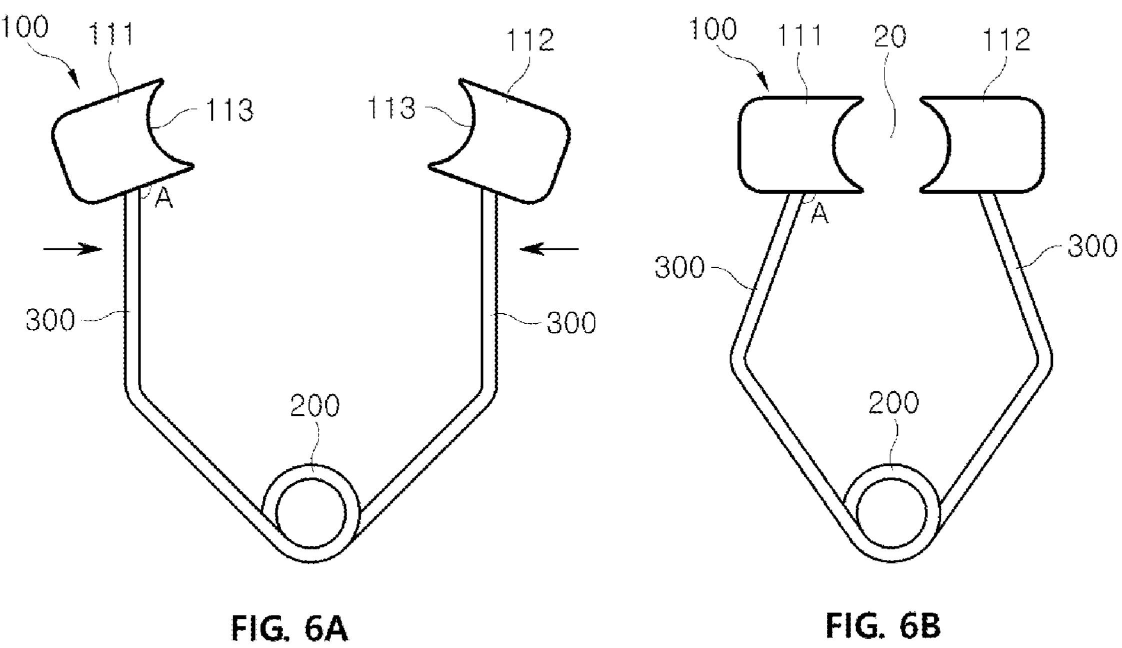
FIG. 6A
FIG. 6B
FIG. 7A
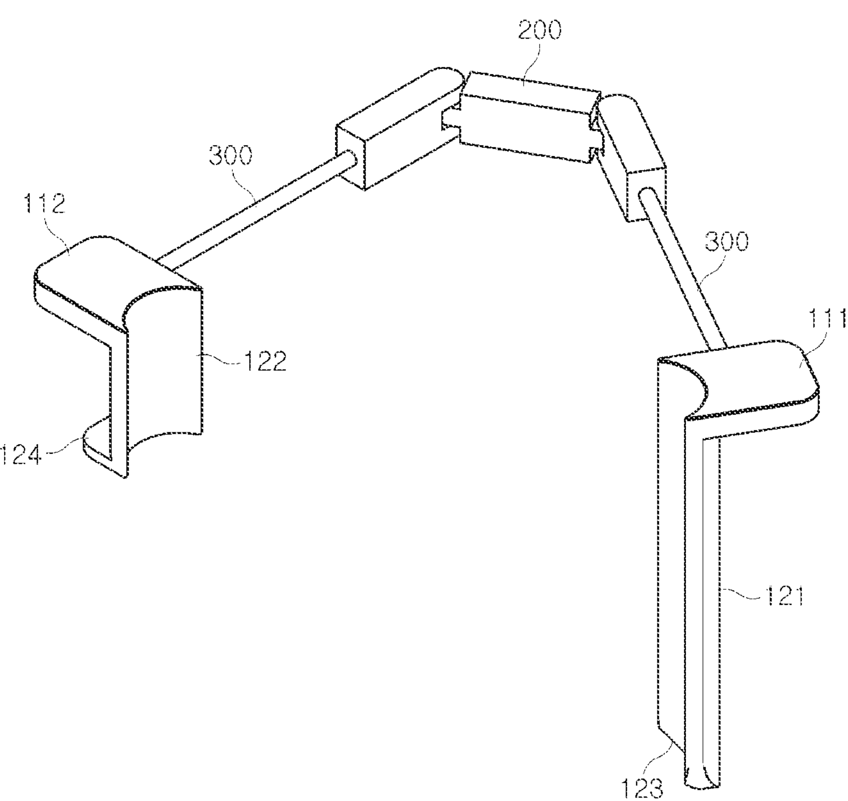

RETRACTOR FOR SPINAL SURGERY

TECHNICAL FIELD

The present invention relates to a spine retractor capable of securing and maintaining a surgery hole at the time of minimally invasive surgery (MIS) for spine disease.

BACKGROUND ART

Minimally invasive surgery (MIS) is a surgical technique in which a surgical instrument is inserted into the body of a patient through a minimal incision portion and surgery is performed, unlike conventional laparotomy, wherein an incision site is small and a bleeding amount is small, whereby recovery is fast, and there is almost no pain or scar after surgery, whereby the number of surgical procedures has increased in recent years.

In recent years, the minimally invasive surgery technique has been used even at the time of spinal surgery. In this case, an incision portion must be formed in order to expose a surgical site, a surgery hole having a predetermined size must be secured such that approach and operation of a surgical instrument are easily performed, and the size of the surgery hole must be maintained uniform during surgery.

Even though the surgery hole is secured so as to have a predetermined size, the surgery hole tends to contract over time due to characteristics of human tissue, and therefore it is necessary to maintain the surgery hole during surgery.

In addition, various kinds of medical instruments are introduced and removed through the surgery hole at the time of spinal surgery, and even after insertion, the medical instrument is used in a mobile state, whereby the medical instrument applies pressure to a portion of the surgery hole and friction occurs between the medical instrument and the surgery hole.

In order to secure and maintain the surgery hole and to minimize pressure applied to the surgery hole by the medical instruments and friction between the surgery hole and the medical instruments, a spine retractor is used in the incision portion.

For a conventional retractor, as shown in FIG. 1, a surgical instrument guide is inserted into an incision portion, and medical staff must continuously pull a handle in order to secure a surgery hole.

Meanwhile, at the time of minimally invasive spine surgery, the medical staff uses not only a medical instrument for surgery but also an endoscope in order to check the interior of the body, wherein the endoscope is not fixed but is continuously moved according to the intention of the medical staff in order to check an insertion process and a lesion.

Since the retractor for securing the surgery hole must also be pulled, as described in this situation, it is very difficult for only a single doctor to simultaneously control the endoscope, the medical instrument, and the retractor.

As described above, the conventional retractor must be continuously pulled by the medical staff. For a retractor other than the pulling type retractor, the size of the retractor is very large or the construction of the retractor is complex in order to fix the retractor, whereby interference with another medical instrument may occur, and therefore convenience in use is very low.

DISCLOSURE

Technical Problem

It is an object of the present invention to provide a spine retractor including an elastic means provided at a main body in order to provide retractive force necessary to maintain a surgery hole, whereby control of the spine retractor by medical staff is not needed, wherein the spine retractor is conveniently installed in the surgery hole, and the construction of the spine retractor is simple.

Technical Solution

In order to accomplish the above object, the present invention provides a spine retractor including a main body fastened to a surgery hole, the main body being configured to maintain the surgery hole, an elastic means configured to provide retractive force necessary to maintain the surgery hole to the main body, and a support member formed between the main body and the elastic means, the support member being configured to transmit the retractive force to the main body.

In addition, the main body may include horizontal retraction portion fastened to an inlet of the surgery hole and a vertical retraction portion inserted into the surgery hole, the vertical retraction portion being coupled to a lower side of the horizontal retraction portion.

In addition, the main body may have an open-shaped guide hole formed by a pair of opposite horizontal retraction portions and a pair of opposite vertical retraction portions.

Here, the horizontal retraction portion may be configured such that a first retraction portion and a second retraction portion are formed so as to be opposite each other, opposite parts of the first retraction portion and the second retraction portion are formed as curved parts, and the curved parts of the first retraction portion and the second retraction portion are converged or diverged to form the open-shaped guide hole according to the retractive force, whereby the inlet of the surgery hole is secured and maintained.

In addition, the support member may be connected to the first retraction portion and the second retraction portion in order to converge the first retraction portion and the second retraction portion to each other by compressive force.

In addition, an angle (A) formed by each of the first retraction portion and the second retraction portion and an inner side of the support member may be $30° \leq A \leq 150°$.

In addition, the horizontal retraction portion may be formed so as to be rotatable or movable relative to the support member.

In addition, the vertical retraction portion may include a third retraction portion and a fourth retraction portion formed respectively at the first retraction portion and the second retraction portion so as to extend perpendicularly therefrom, wherein the third retraction portion may be provided at a lower end thereof with an inclined portion, and the fourth retraction portion may be further provided at a lower end thereof with a catching protrusion.

In addition, each of the third retraction portion and the fourth retraction portion may be further provided at an outer surface thereof abutting a human body with a friction portion.

Meanwhile, the elastic means may be formed as a coiled spring formed continuous with the support member, or the elastic means may be formed as a spring type hinge connected to the support member.

Advantageous Effects

The present invention relates to a spine retractor capable of securing and maintaining a surgery hole at the time of minimally invasive surgery (MIS) for spine disease, wherein an elastic means configured to to maintain the provide retractive force necessary surgery hole is provided at a main body, whereby control of the spine retractor by medical staff is not needed, the spine retractor is conveniently installed in the surgery hole, and the construction of the spine retractor is simple, whereby there is little interference with another medical instrument, and therefore convenience in use is improved.

In addition, the present invention serves to protect an inner wall and an inlet of the surgery hole, whereby it is possible to minimize damage to tissue at the inner wall of the surgery hole due to a surgical instrument and friction between the surgery hole and the medical instrument.

Also, in the present invention, an open-shaped guide hole is formed, whereby it is possible to secure a surgery hole optimized for surgery and to enable the retractor to be stably fixed to any of various shaped surgery holes, and therefore convenience in use is further improved.

In addition, the present invention serves to guide stable insertion of the surgical instrument, whereby it is possible to enable a beginner doctor to successfully use the surgical instrument, and the present invention also serves as guide for securing the field of view of medical staff using microscopy.

DESCRIPTION OF DRAWINGS

FIGS. 6A and 6B are schematic views showing operation according to another embodiment of the present invention.

FIGS. 7A, 7B, 8A and 8B are schematic views of a further embodiment of the present invention.

BEST MODE

The present invention relates to a spine retractor capable of securing and maintaining a surgery hole at the time of minimally invasive surgery (MIS) for spine disease, wherein an elastic means configured to provide retractive force necessary to maintain the surgery hole is provided at a main body, whereby control of the spine retractor by medical staff is not needed, the spine retractor is conveniently installed in the surgery hole, and the construction of the spine retractor is simple, whereby there is little interference with another medical instrument.

Figure 1:
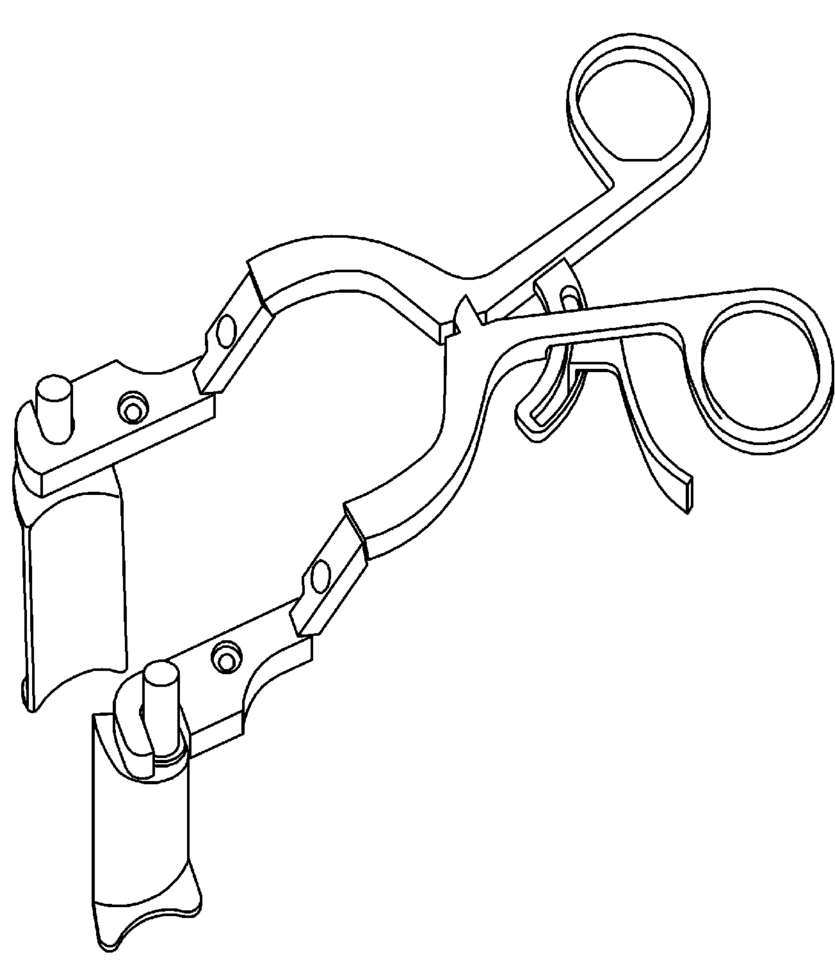
FIG. 1 is a schematic view of a conventional retractor for surgery.
Figure 2:
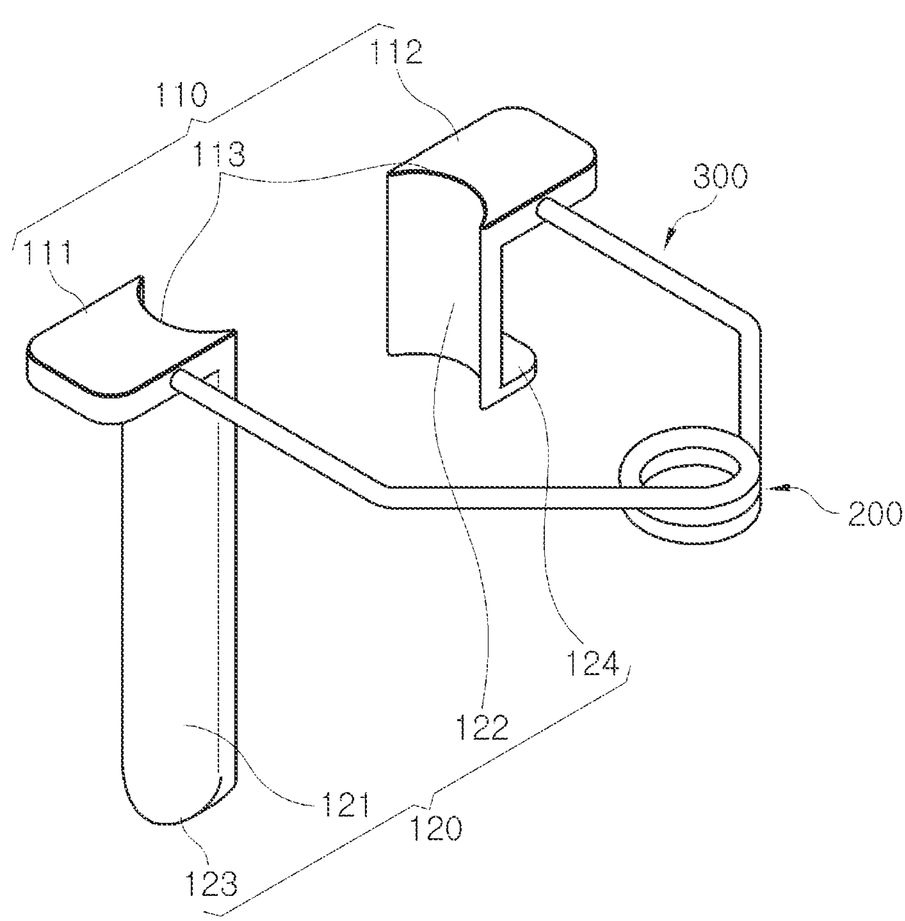
FIG. 2 is a perspective view of a spine retractor according to an embodiment of the present invention.
Figure 3:
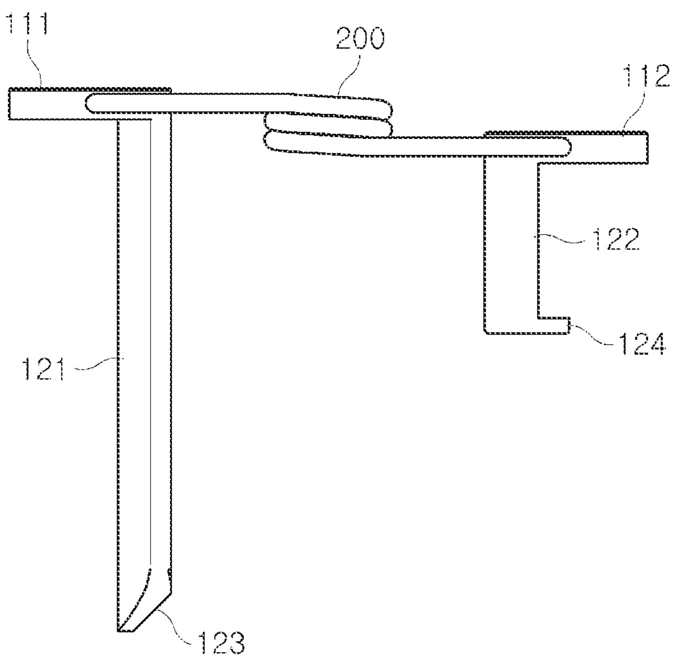
FIG. 3 is a side view of the spine retractor according to the embodiment of the present invention.
Figure 4:
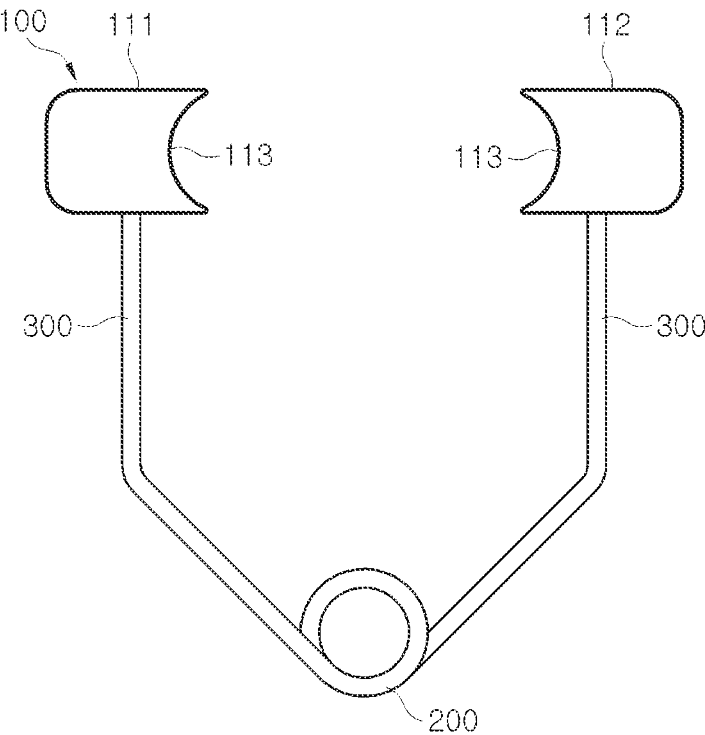
FIG. 4 is a plan view of the spine retractor according to the embodiment of the present invention.
Figures 5A, 5B, 5C:
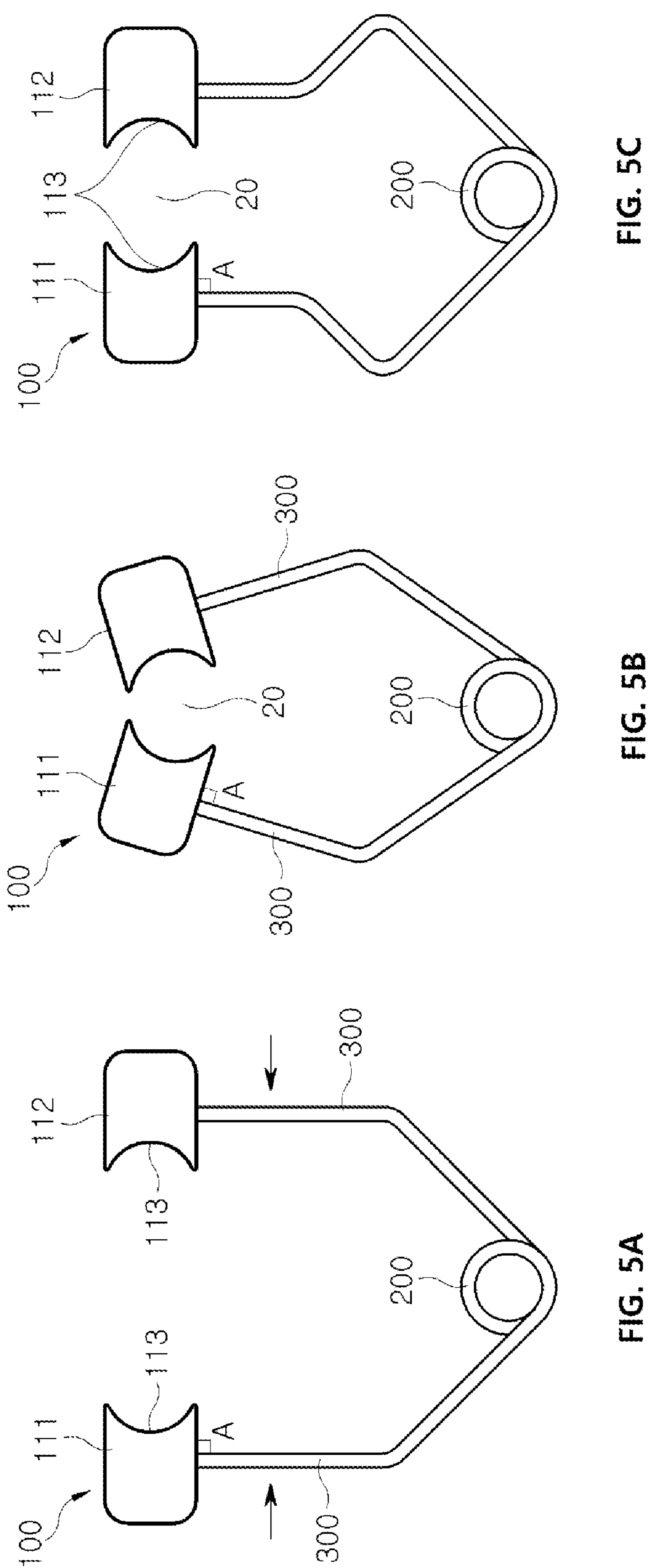
FIGS. 5A, 5B and 5C are schematic views showing operation according to an embodiment of the present invention.

Hereinafter, the present invention will be described in detail with reference to the accompanying drawings. FIG. 2 is a perspective view of a spine retractor according to an embodiment of the present invention, FIG. 3 is a side view of the spine retractor according to the embodiment of the present invention, FIG. 4 is a plan view of the spine retractor according to the embodiment of the present invention, FIGS. 5A, 5B and 5C are schematic views showing operation according to an embodiment of the present invention, FIGS. 6A and 6B are schematic views showing operation according to another embodiment of the present invention, FIGS. 7 and 8 are schematic views of a further embodiment of the present invention, and FIGS. 9A and 9B are schematic views showing actual application of the embodiment of the present invention.

As shown, the spine retractor according to the present invention generally includes a main body 100 fastened to a surgery hole 10, the main body being configured to maintain the surgery hole 10, an elastic means 200 configured to provide retractive force necessary to maintain the surgery hole 10 to the main body 100, and a support member 300 formed between the main body 100 and the elastic means 200, the support member being configured to transmit the retractive force to the main body 100.

First, the main body 100 is fastened to the surgery hole 10 and is inserted into the surgery hole 10 while being fastened to an inlet of the surgery hole 10 in order to secure and maintain the surgery hole 10, wherein the main body includes a horizontal retraction portion 110 fastened to the inlet of the surgery hole 10 and a vertical retraction portion 120 inserted into the surgery hole 10, the vertical retraction portion being coupled to a lower side of the horizontal retraction portion 110.

The main body 100 serves to retract and hold the surgery hole 10 in order to maintain the inlet and an interior of the surgery hole so as to have predetermined shapes and sizes, wherein an open-shaped guide hole 20 is formed by a pair of opposite horizontal retraction portions 110 and a pair of opposite vertical retraction portions 120, whereby it is possible to secure the surgery hole 10 so as to have a desired size and shape and to maintain the state of the surgery hole without being greatly influenced by the size and shape of the surgery hole 10.

Specifically, the horizontal retraction portion 110 of the main body 100 is fastened to the inlet of the surgery hole 10, wherein the pair of opposite horizontal retraction portions 110, i.e. a first retraction portion 111 and a second retraction portion 112, are formed so as to be opposite each other, whereby an inlet of the open-shaped guide hole 20 is formed.

More specifically, opposite parts of the first retraction portion 111 and the second retraction portion 112 are formed as curved parts 113, wherein the curved parts 113 of the first retraction portion 111 and the second retraction portion 112 are converged or diverged to form the open-shaped guide hole 20 according to the retractive force, whereby it is possible to maintain the inlet of the surgery hole 10 so as to have a circular shape, an oval shape, or a shape necessary for the surgery hole 10.

That is, the first retraction portion 111 and the second retraction portion 112 move close to each other (convergence) or move away from each other (divergence) according to the retractive force, whereby it is possible to easily adjust the size of the guide hole 20 depending on a surgical site or the size of the surgery hole 10. As a result, it is possible to apply the main body to the surgery hole 10 irrespective of the size of the surgery hole, and therefore it is possible to apply the main body to various surgical sites or various sizes of surgery holes 10. Consequently, the retractor according to the present invention is coupled to an inner wall of the surgery hole 10 in tight contact therewith, and therefore it is possible to stably secure and maintain the surgery hole 10.

In addition to securing and maintaining the surgery hole 10, the guide hole 20 serves to protect the inner wall and the inlet of the surgery hole 10, whereby it is possible to minimize friction between the inner wall of the surgery hole 10 and a surgical instrument and damage to tissue at the inner wall of the surgery hole due to the surgical instrument.

In addition, the guide hole 20 serves to guide the surgical instrument so as to be stably inserted, whereby it is possible to enable a beginner doctor to successfully use the surgical instrument, and also serves as a guide for securing the field of view of medical staff using microscopy.

In addition, each of the curved parts 113 of the first retraction portion 111 and the second retraction portion 112 is formed so as to have a radius of curvature of about 5 to 20 mm, whereby the guide hole 20 is implemented so as to have a circular shape or an oval shape depending on the surgery hole 10 or the retractive force, and therefore it is possible to faithfully perform a guide role for insertion of the surgical instrument with minimized interference with the surgical instrument.

The vertical retraction portion 120, which is inserted into the surgery hole 10, is coupled to the lower side of the horizontal retraction portion 110, wherein the vertical retraction portion includes a third retraction portion 121 and a fourth retraction portion 122 formed respectively at the first retraction portion 111 and the second retraction portion 112 so as to extend perpendicularly therefrom.

The third retraction portion 121 and a fourth retraction portion 122 are formed so as to have predetermined lengths in order to secure the surgery hole 10 depending on the surgical site and the type of surgery, thereby securing and maintaining the surgery hole 10 in a (perpendicular) longitudinal direction, and are interlocked respectively with the first retraction portion 111 and the second retraction portion 112 so as to be retracted together with the first retraction portion and the second retraction portion when the first retraction portion and the second retraction portion are retracted.

Specifically, the third retraction portion 121 and the fourth retraction portion 122 are formed so as to extend perpendicularly along the shapes of the curved parts 113 of the first retraction portion 111 and the second retraction portion 112, and therefore the third retraction portion 121 and the fourth retraction portion are formed so as to extend while having the curved shapes of the first retraction portion 111 and the second retraction portion 112. That is, in general, the surgery hole 10 is configured to have the shape of a cylinder or an oval column that is perpendicularly long, and therefore interference with the surgical instrument is minimized when the surgical instrument is inserted, the surgical instrument is easily inserted, and it is structurally easy to secure the field of view.

As needed, the third retraction portion 121 and the fourth retraction portion 122 may be formed so as to have the same length, or any one thereof may be formed so as to be shorter or longer. That is, design change is possible so as to easily guide the third retraction portion and the fourth retraction portion depending on a surgery environment, the surgical site, or the kind of the surgical instrument.

In an embodiment, the third retraction portion 121 is formed so as to be longer than the fourth retraction portion 122, an inclined portion 123 is formed at a lower end of the third retraction portion 121 so as to be easily inserted into the surgery hole 10, and a catching protrusion 124 is formed a lower end of the fourth retraction portion 122 so as to easily fix the retractor and to prevent contraction of the surgery hole 10.

In addition, it is preferable for a friction portion to be further formed at an outer surface of each of the third retraction portion 121 and the fourth retraction portion 122, which contacts the human body. The friction portion may be implemented by curving the surface of each of the third retraction portion 121 and the fourth retraction portion 122, or may be implemented so as to have the shape of a protrusion that causes friction. The friction portion is coupled to the inner wall of the surgery hole in order to prevent unintentional separation of the retractor according to the present invention from the surgery hole, and is fixed in position in order to prevent movement of the retractor during surgery.

The fourth retraction portion 122 is formed so as to have an appropriate length such that the catching protrusion 124 is caught by tissue around the surgical site. The catching protrusion 124 is formed in a direction parallel to the retractive force, whereby the catching protrusion is fixed to tissue around the surgery hole 10 together with the second retraction portion 112, and therefore it is possible to strongly fix the retractor even when friction or movement occurs during surgery and to easily fix the retractor.

Retractive force necessary to secure and maintain the surgery hole 10 is provided from the elastic means 200 to the horizontal retraction portion 110 and the vertical retraction portion 120 of the main body 100, and the support member 300 is formed between the main body 100 and the elastic means 200 to transmit the retractive force from the elastic means 200 to the main body 100.

The elastic means 200 may be formed as a coiled spring formed continuous with the support member 300, as shown in FIGS. 2 to 6, or may be formed as a spring type hinge connected to the support member 300, as shown in FIGS. 7 and 8.

The support member 300 is connected to the main body 100, i.e. the first retraction portion 111 and the second retraction portion 112 of the horizontal retraction portion 110, to converge the first retraction portion 111 (the third retraction portion 121) and the second retraction portion 112 (the fourth retraction portion 122) to each other by compressive force.

As shown in FIGS. 5 and 6, when the medical staff applies predetermined compressive force to the support member 300 (FIGS. 5(*a*) and 6(*a*)), the support member 300 is curved or bent by the elastic member 200, whereby the first retraction portion 111 (the third retraction portion 121) and the second retraction portion 112 (the fourth retraction portion 122) are converged to each other (FIGS. 5(*b*), 5(*c*), and 6(*b*)). When the compressive force is released after the retraction portions are inserted into the surgery hole 10 from the inlet of the surgery hole 10, the support member 300 is brought into tight contact with the inner wall of the surgery hole 10 by retractive force (opposite to the compressive force) transmitted via the coiled spring or the spring type hinge, whereby the surgery hole 10 is secured and maintained.

FIGS. 5A, 5B and 5C show the case in which an angle A formed by the support member 300 and the horizontal retraction portion 110 is a right angle (90 degrees), wherein the shape of the guide hole 20 may be changed depending on a direction of the compressive force applied to the support member 300, and therefore it is possible for a user to appropriately select the shape of the guide hole and to use the guide hole having the selected shape depending on the surgery environment.

FIGS. 6A and 6B show the case in which the angle formed by the support member 300 and the horizontal retraction portion 110 is greater than 90 degrees, wherein the guide hole 20 is configured to have a shape similar to a circular shape so as to be applied to the surgery hole 10 when compressive force is applied to the support member 300.

Specifically, the angle A formed by each of the first retraction portion 111 and the second retraction portion 112 and an inner side of the support member 300 is defined as follows: 30°≤A≤150°. When the first retraction portion 111 and the second retraction portion 112 are converged to each other by the compressive force of the support member 300, therefore, it is possible to configure the inlet of the guide hole 20 (the inlet of the surgery hole 10) so as to have any of various shapes, such as a circular shape or an oval shape.

In addition, the first retraction portion 111 and the second retraction portion 112 are formed so as to be rotatable or movable relative to the support member 300 in order to adjust the shape and size of the inlet of the guide hole 20, whereby application to various surgical environments is possible.

The support member 300 may be made of a material configured such that appropriate compressive force is applicable to the support member and refractive force by the elastic means 200 is transmittable to the support member, i.e. a material that is hardly deformed even though compressive force and retractive force are repeatedly applied thereto, such as a metal material. In addition, the support member is formed so as to have a predetermined length such that appropriate compressive force and retractive force are transmitted thereto.

That is, the angle between the support member 300 and the horizontal retraction portion 110 and the distance between the first retraction portion 111 and the second retraction portion 112 are adjusted based on the shape of the surgery hole 10 depending on the surgery environment, whereby it is possible to secure a surgery hole 10 most preferable for surgery and to stably fix the retractor in any one of various shaped surgery holes 10.

Meanwhile, any means capable of providing retractive force necessary to maintain the surgery hole 10 to the main body 100 may be used as the elastic means 200 according to the present invention. Preferably, however, the embodiment, such as the coiled spring or the spring type hinge, described above may be applied.

For the coiled spring shown in FIGS. 2 to 6, the size or the modulus of elasticity of the spring may be adjusted in order to adjust the magnitude of retractive force, and the retractive force is applied in a direction in which compressive force of the support member 300 is released by elastic force of the spring.

Figure 7B:
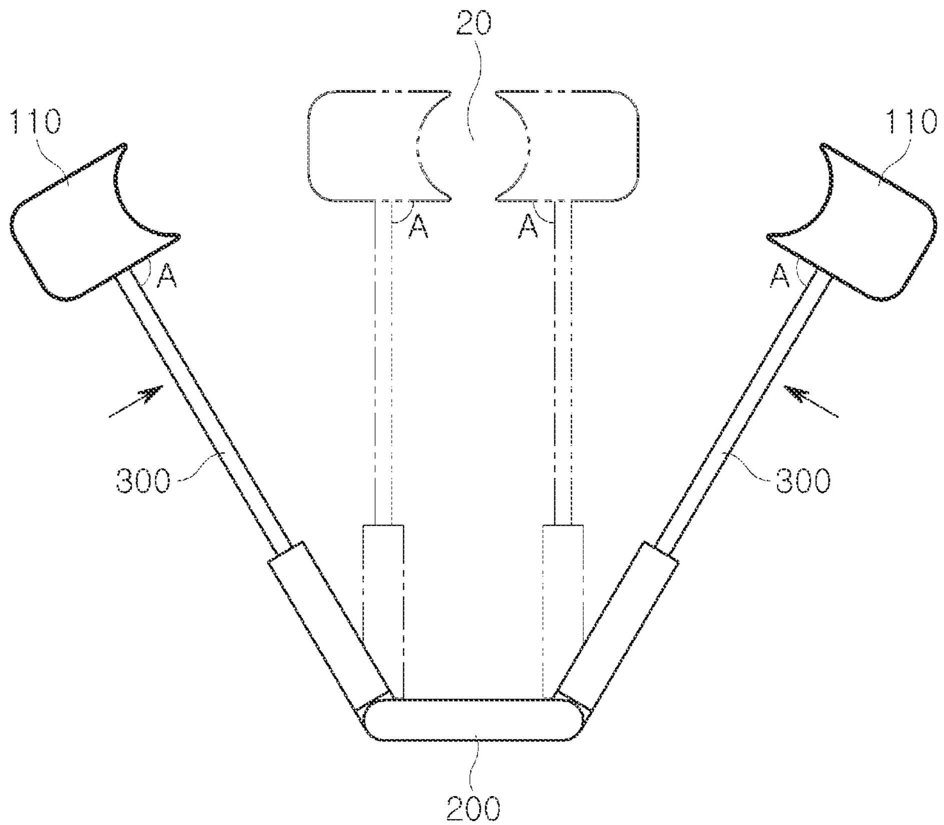
Figure 8A:
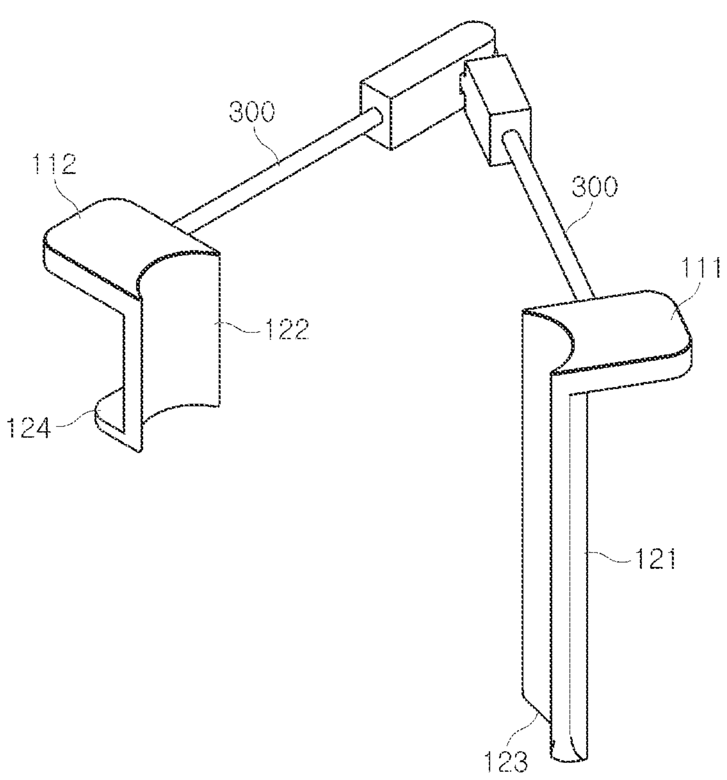
Figure 8B:
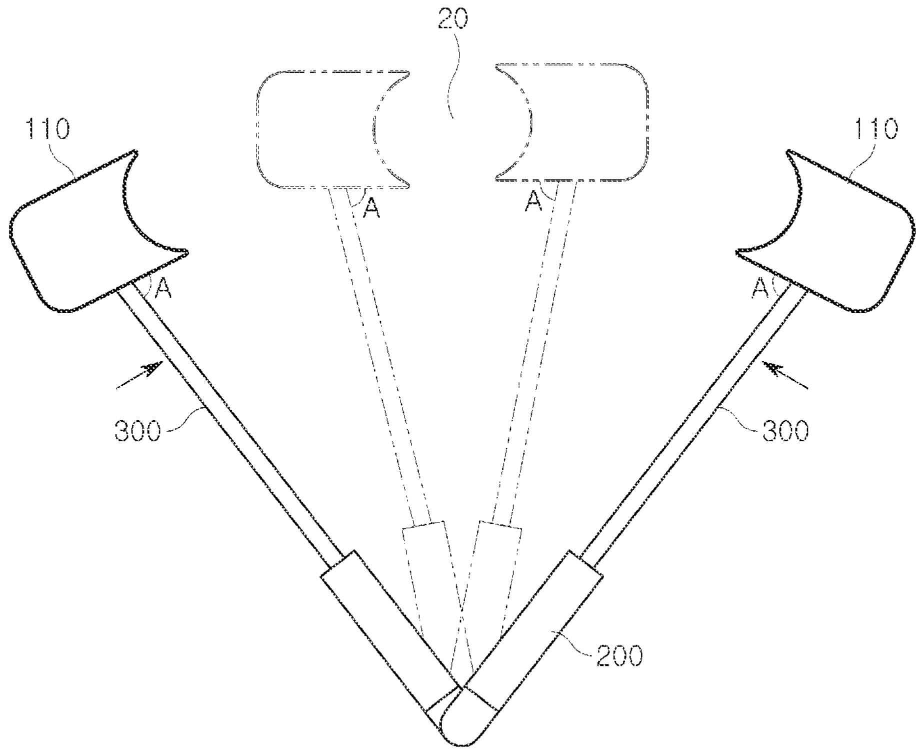
Figure 9A:
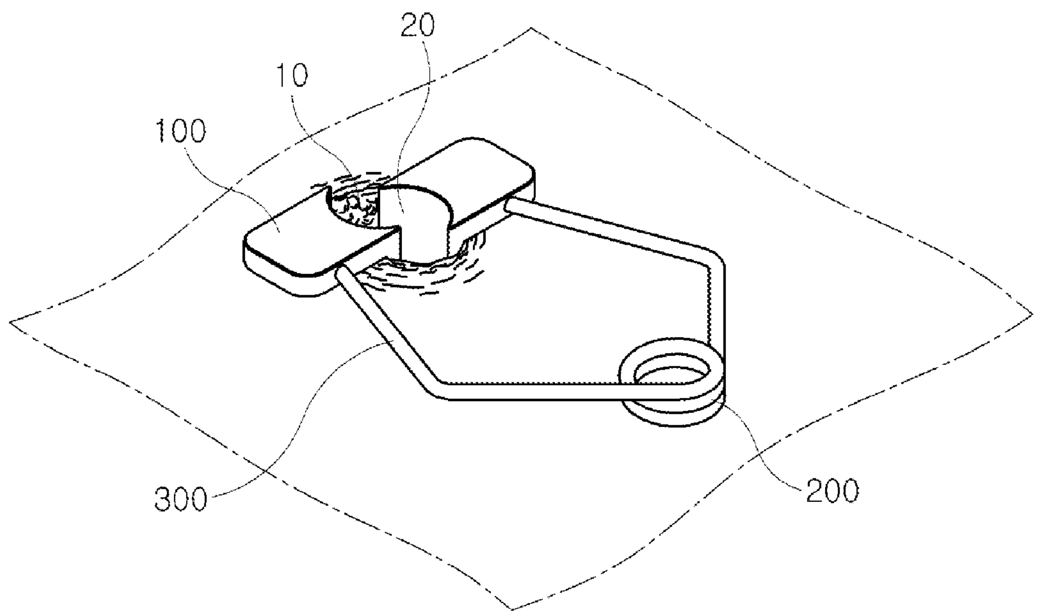
FIGS. 9A and 9B are schematic views showing actual application of the embodiment of the present invention.
Figure 9B:
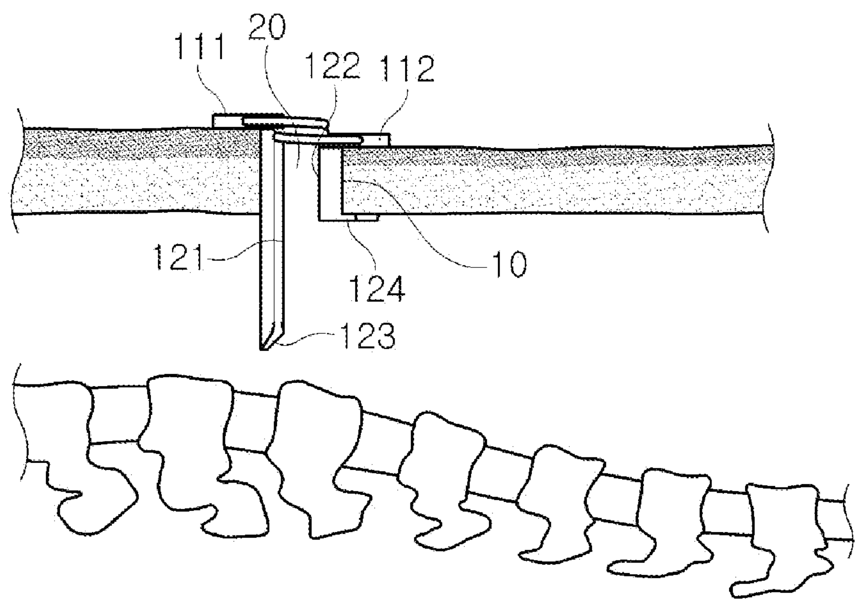

For the spring type hinge shown in FIGS. 7 and 8, in which a three-stage spring type hinge (FIGS. 7A and 7B) or a two-stage spring type hinge (FIGS. 8A and 8B) is shown, a spring is mounted in the hinge such that retractive force acts, and the retractive force is applied in a direction in which compressive force of the support member 300 is released by elastic force of the spring.

FIG. 7A is an overall perspective view of the three-stage spring type hinge, and FIG. 7B is a schematic view showing operation of the three-stage spring type hinge. When compressive force is applied to the support member 300, the main body 100 is converged (narrowed) by the hinge. When the compressive force is released, the main body 100 is diverged (widened) by the hinge.

FIG. 8A is an overall perspective view of the two-stage spring type hinge, and FIG. 8B is a schematic view showing operation of the two-stage spring type hinge. When compressive force is applied to the support member 300, the main body 100 is converged by the hinge. When the compressive force is released, the main body 100 is diverged by the hinge.

FIGS. 9A and 9B are schematic views showing the state in which the retractor according to the present invention is applied to a surgical site. It is possible for the medical staff to fix the retractor to the surgery hole 10 without independent handling of the retractor, whereby it is possible to easily secure and maintain the surgery hole 10, and therefore it is possible to greatly improve convenience in use of the medical staff.

In addition, a construction for securing and maintaining the surgery hole 10 is very simple, and the retractor is small, whereby it is possible to minimize interference with another medical instrument, and therefore convenience in use is further improved.

The invention claimed is:

1. A spine retractor comprising:

a main body configured to be fastened to a surgery hole and to maintain the surgery hole, the main body comprising:

a horizontal retraction portion configured to be fastened to an inlet of the surgery hole; and a vertical retraction portion configured to be inserted into the surgery hole, the vertical retraction portion being coupled to a lower side of the horizontal retraction portion, wherein:

the horizonal retraction portion is formed by a pair of opposite horizontal retraction portions and the vertical retraction portion is formed by a pair of opposite vertical retraction portions, the pair of opposite horizontal retraction portions comprising a first retraction portion and a second retraction portion that are formed to be opposite of each other, and each of the first retraction portion and the second retraction portion have an opposite part formed as a concave curved part configured to oppositely face each other, and the pair of vertical retraction portion comprises a third retraction portion and a fourth retraction portion formed respectively at the first retraction portion and the second retraction portion so as to extend perpendicularly therefrom along each concave curved part of the first retraction portion and the second retraction portion;

an elastic body configured to provide retractive force necessary to maintain the surgery hole to the main body; and a support member formed between the main body and the elastic body, the support member being configured to transmit the retractive force from the elastic body to the main body, wherein each of the first retraction portion and the second retraction portion extends in a horizontal direction and has a width greater than a diameter of the support member, and wherein the elastic body is formed as a coiled spring formed continuous with the support member or as a spring type hinge connected to the support member, and the coiled spring or the spring type hinge is configured to pull the first and second retraction portions away from each other with its elastic force.

2. The spine retractor according to claim 1, wherein the main body has an open-shaped guide hole formed by the pair of opposite horizontal retraction portions and the pair of opposite vertical retraction portions.

3. The spine retractor according to claim 2, wherein the curved parts of the first retraction portion and the second retraction portion of the pair of opposite horizontal retraction portions are converged or diverged to form the open-shaped guide hole according to the retractive force, whereby the inlet of the surgery hole is secured and maintained.

4. The spine retractor according to claim 3, wherein the support member is connected to the first retraction portion and the second retraction portion in order to converge the first retraction portion and the second retraction portion to each other by compressive force.

5. The spine retractor according to claim 4, wherein an angle (A) formed by each of the first retraction portion and the second retraction portion and an inner side of the support member is $30° \leq A \leq 150°$.

6. The spine retractor according to claim 5, wherein the horizontal retraction portion is formed so as to be rotatable or movable relative to the support member.

7. The spine retractor according to claim 3, wherein the third retraction portion is provided at a lower end thereof with an inclined portion.

8. The spine retractor according to claim 3, wherein the fourth retraction portion is further provided at a lower end thereof with a catching protrusion.

9. The spine retractor according to claim 3, wherein each of the third retraction portion and the fourth retraction portion has a friction portion formed at an outer surface of each of the third retraction portion and the fourth retraction portion, which is configured to abut a human body.

10. The spine retractor according to claim 1, wherein the third retraction portion and the fourth retraction portion have different lengths and different structures.

* * * * *